(12) United States Patent
Grant et al.

(10) Patent No.: US 10,684,293 B2
(45) Date of Patent: Jun. 16, 2020

(54) ASSOCIATING SOMATIC GENE MUTATIONS IN GLYCOPHORIN A WITH COMPLEX MULTIFACTORIAL DISEASES

(71) Applicant: NOVA SOUTHEASTERN UNIVERSITY, Fort Lauderdale, FL (US)

(72) Inventors: Stephen G. Grant, Fort Lauderdale, FL (US); Jean J. Latimer, Fort Lauderdale, FL (US)

(73) Assignee: NOVA SOUTHEASTERN UNIVERSITY, Fort Lauderdale, FL (US)

( * ) Notice: Subject to any disclaimer, the term of this patent is extended or adjusted under 35 U.S.C. 154(b) by 422 days.

(21) Appl. No.: 14/892,682

(22) PCT Filed: May 27, 2014

(86) PCT No.: PCT/US2014/039626
§ 371 (c)(1),
(2) Date: Nov. 20, 2015

(87) PCT Pub. No.: WO2014/190358
PCT Pub. Date: Nov. 27, 2014

(65) Prior Publication Data
US 2016/0109468 A1   Apr. 21, 2016

Related U.S. Application Data

(60) Provisional application No. 61/827,420, filed on May 24, 2013.

(51) Int. Cl.
*G01N 33/80* (2006.01)
*G01N 33/50* (2006.01)

(52) U.S. Cl.
CPC ......... *G01N 33/80* (2013.01); *G01N 33/5005* (2013.01); *G01N 33/5091* (2013.01);
(Continued)

(58) Field of Classification Search
CPC .... G01N 33/80; G01N 33/92; G01N 33/5302; G01N 33/555; G01N 15/14;
(Continued)

(56) References Cited

U.S. PATENT DOCUMENTS 7,824,874 B2   11/2010   Dertinger

FOREIGN PATENT DOCUMENTS

WO   2013156806   10/2013
WO   2014190358   11/2014

OTHER PUBLICATIONS

Langois et al. An Improved Flow Cytometric Assay for Somatic Mutations at the Glycophorin A Locus in Humans. Cytometry 11: 513-521 (1990)—IDS.*

(Continued)

*Primary Examiner* — Gailene Gabel
(74) *Attorney, Agent, or Firm* — Fleit Intellectual Property Law; Paul D. Bianco; Katherine Davis Wong (57) ABSTRACT

In the detection of a complex multifactorial disease, an MN blood group typing is performed on a first blood sample of a subject to be tested for a complex multifactorial disease, and on a second blood sample of a control subject having known phenotypes. Erythrocytes from the samples are isovolumetrically sphered, and M alleles and N alleles expressed on surfaces of erythrocyte cells of the first and second blood samples are labeled by contacting the blood samples with anti-M antibodies and anti-N antibodies associated with a marker. Labeled M alleles and labeled N alleles in the first and second blood samples are detected and quantified using the marker, in order to determine an inci- (Continued)

dence of somatic mutations in Glycophorin A of the patient. The incidence is compared with data pertaining to patients with a known complex multifactorial disease, to diagnose the patient.

26 Claims, 5 Drawing Sheets

(52) U.S. Cl.
CPC .................. *G01N 33/5094* (2013.01); *G01N 2333/70596* (2013.01); *G01N 2800/28* (2013.01)

(58) Field of Classification Search
CPC ........... G01N 15/1402; G01N 33/5005; G01N 33/5091; G01N 33/5094; G01N 2333/70596; G01N 2800/28
See application file for complete search history.

(56) References Cited

OTHER PUBLICATIONS

Grant. Tobacco Smoke Exposure and Somatic Mutations in Newborn. The Open Pediactric Medicine Journal 4: 10-13 (2010)—IDS.*
Rothman et al. Benzene induces gene-duplicating but not gene-inactivating mutations at the glycophorin A locus in exposed humans. Proc. Natl. Acad. Sci. 92: 4069-4073 (Apr. 1995).*
Grant, Stephen G. The GPA in Vivo Somatic Mutation Assay. Methods of Molecular Biology 291: 179-195 (2005).*
International Search Report dated Oct. 9, 2014 for PCT/US114/039626 filed May 27, 2014.
Written Opinion dated Oct. 9, 2014 for PCT/US114/039626 filed May 27, 2014.
Langois et al., An lymphoImprovement Flow cytometric assay for somatic mulattions at the glycophorin a lucus in humans, vol. 11 No. 4. pp. 513-521, Cytomatry 1990.
Bell et al. The Fatty compositions of erythrocyte and plasma polar lipids in children with autism, developmental delay or typically developing controls and the effect of fish oil intake, vol. 103, pp. 1160-1167, The Authors 2009.
Ciccoli et al. Erythrocyte shape abnormalities, membrane oxidative damage, and actin alterations: An unrecognized triad in classical autism, Hindawl Publishing Corp., Mediators of Inflammation, Article ID 432616, 2013.
Bigbee et al., Human in vivo somatice mutation measured at two loci: individuals with stably elevated background erythrocyte glycophorin A (gpa) variant frequencies exhibit normal t-lymphocayte hprt mutant frequencies, 2;397(2);119-36, PubMed Feb. 1998. abstract, Abstract Only.
R.J. Albertini et al., In vivo somatice cell gene mutations in human, University of Vermont, book 9 , pp. 118-139, retrieved May 23, 2013.
Definition of "glycophorin" from Wikipedia Encyclopedia—http://en.wikipedia.org/wiki/Glycophorin—retrieved May 23, 2013.
Definition of "glycophorin A" as obtained from the gene data base of the National Institute of Health (NIH)—http://www.ncbi.nlm.nih.gov/gene/2993—retrieved May 23, 2013.
Grant, The GPA in vivo somatic mutation assay, Methods of Molecular Biology, Mol Biol 291:179-195 2005; 291:179-95, abstract—retrieved May 23, 2013.
Grant, The GPA in vivo somatic mutation assay, summary—Methods of Molecular Biology, book 18, vol. 291, p. 179, retrieved May 23, 2013, Abstract only.
Grant, Translating mutagenesls into carcinogenesis, ISSN:2157-2518, vol. 3, Issue 1, 2012.
Grant, Tobacca smoke exposure and somatic mutation in newborns, The Open Pediatric Medicine Journal, 2010.
N. Rothman et al., Benzene induces gene-duplication but not gene-inactivatiin mutations at the glycophorin A lucus in exposed humans, Proc. Nat. Acad. Sci., vol. 92, pp. 4069-4073 Apr. 1995.

\* cited by examiner

ASSOCIATING SOMATIC GENE MUTATIONS IN GLYCOPHORIN A WITH COMPLEX MULTIFACTORIAL DISEASES

FIELD OF THE INVENTION

The invention relates to the study of in vivo somatic cell gene mutations and similar events, particularly to analysis of allele loss, recombination, somatic mutation and epigenetic gene inactivation in complex, multifactorial diseases, and most particularly to an assay for detection and quantification of Glycophorin A (GPA) somatic mutations and their frequency in autistic and cancer patients.

BACKGROUND

A "gene mutation" is considered to be any heritable change in the genetic code. Mutations are very rare events, on the order of one per million per cells per locus.

A number of gene-specific assays have been developed for measurement of human somatic mutations. Such assays provide a detection system that can detect and quantify rare mutations. These assays normally require access to a large quantity of cells and a reporter locus where mutations can be easily measured. One applied assay is the Glycophorin A (GPA) in vivo somatic mutation assay. See Chapter 9, section 9.2.3 of *Methods to Assess DNA Damage and Repair: Interspecies Comparisons*, edited by R. G. Tardiff et al., published by John Wiley & Sons Ltd, 1994.

A glycophorin is a sialoglycoprotein of the membrane of the red blood cell (also identified as RBC or erythrocyte). It is a membrane-spanning protein carrying sugar molecules; i.e. it is heavily glycosylated (~60%). Glycophorins are rich in sialic acid, which gives the red blood cells a very hydrophilic-charged cell surface. This enables the cells to circulate without adhering to the vessel walls. Definition of "glycophorin" as obtained from Wikipedia on May 23, 2013, which is incorporated herein by reference.

Glycophorin A (also identified as GYPA or GPA) is the major and most abundant sialoglycoprotein of the erythrocyte membrane and bears the antigenic determinant for the MN blood group. The M and N antigens commonly occur in all populations. Definition and sequence listing of "glycophorin A" as obtained from the gene data base of the National Institute of Health (NIH) on May 23, 2013, which is incorporated herein by reference.

The autosomal gene for Glycophorin A is located at the distal end of chromosome 4. This gene is the genetic determinant of the MN blood group. Two common alleles, M and N both present at frequencies ~50% on red blood cells. The M and N forms of the Glycophorin A protein differ by two non-adjacent amino acids and are concomitantly expressed. See Chapter 9 section 9.2.3 of *Methods to Assess DNA Damage and Repair: Interspecies Comparisons*, edited by R. G. Tardiff et al., published by John Wiley & Sons Ltd, 1994, which is incorporated herein by reference. Monoclonal antibodies have been developed that distinguish between the allelic M and N forms of the Glycophorin A protein.

SUMMARY OF THE INVENTION

In accordance with the disclosure, a method for detection of a complex multifactorial disease, comprises performing an MN blood group typing on a first blood sample of a subject to be tested for a complex multifactorial disease, and on a second blood sample of a control subject having known phenotypes; isovolumetrically sphering the first and second blood samples; labeling M alleles and N alleles expressed on surfaces of erythrocyte cells of the first and second blood samples by contacting the blood samples with anti-M antibodies and anti-N antibodies; detecting and quantifying labeled M alleles and labeled N alleles in the first and second blood samples; obtaining comparison data pertaining to comparing labeled M alleles and labeled N alleles found in the first blood sample to labeled M alleles and labeled N alleles found in the second blood sample; obtaining quantifying data pertaining to detecting and quantifying cells with variant phenotypes consistent with somatic mutations in Glycophorin A, using the comparison data; and comparing the quantifying data with quantifying data of subjects having a known complex multifactorial disease, to determine if the subject to be tested may have the known complex multifactorial disease.

In various embodiments thereof, detecting and quantifying labeled M alleles and labeled N alleles is carried out by using flow cytometry; labeling M alleles and N alleles expressed on surfaces of the erythrocyte cells includes using fluorescently-labeled anti-M antibodies and fluorescently-labeled anti-N antibodies; the first and second blood samples are obtained from subjects age-matched with the subjects having a known complex multifactorial disease; somatic mutations in Glycophorin A include loss of one Glycophorin A allele; somatic mutations in Glycophorin A include loss or functional inactivation of one Glycophorin A allele and duplication of a remaining Glycophorin A allele; and/or somatic mutations in Glycophorin A include loss of expression of one Glycophorin A allele or the functional mimicking of this event via epigenetic allele-specific gene inactivation.

In additional variations thereof, the quantifying data includes data pertaining to mutation frequency of Glycophorin A alleles; quantifying data includes data pertaining to cells with variant allele-loss phenotypes; detecting somatic mutations includes quantifying cells with somatic mutation; the complex multifactorial disease is a DNA repair deficiency disease; the complex multifactorial disease is an autism spectrum disorder; the complex multifactorial disease is cancer.

In a further embodiment of the disclosure, a method for diagnosis of a complex multifactorial disease in a patient, comprises (a) labeling alleles, expressed on surfaces of sample erythrocyte cells removed from the patient, by contacting the blood samples with antibodies bindable to the expressed alleles, the antibodies associated with a machine detectable marker; (b) obtaining patient mutation data corresponding to detecting mutation of the alleles, by quantifying at least one of allele loss and allele loss and duplication events, by measuring the presence of the marker using a machine configured for detecting the presence of the marker associated with the antibodies that have bound to the sample erythrocyte cells; and (c) comparing the patient mutation data with known mutation data obtained using steps (a) and (b), but using erythrocyte cells removed from patients having a known complex multifactorial disease, to diagnose the known complex multifactorial disease in the patient.

In various embodiments thereof, diagnosing the complex multifactorial disease includes determining at least one of the probability, existence, or extent of the multifactorial disease in the patient; the machine is a flow cytometer; the machine is configured to detect the presence of the one or more markers at a frequency of at least 10,000 cells per second; the machine detectable marker is a fluorophore; the complex multifactorial disease is one of autism and cancer; the allele is at least one of M allele and N allele; the patients and patients having a known complex multifactorial disease are age matched within a predetermined age range; and/or the allele corresponds to Glycophorin A.

In various further embodiments thereof, the mutation is at least one of genetic and epigenetic; the mutation is epigenetic, and the complex multifactorial disease is autism; and/or the mutations is caused by exposure to benzene.

In another embodiment of the disclosure, a method for diagnosis of a complex multifactorial disease in a patient, comprises (a) labeling M alleles and N alleles, expressed on surfaces of sample erythrocyte cells removed from the patient, by contacting the blood samples with anti-M antibodies and anti-N antibodies, the anti-M and anti-N antibodies each associated with a fluorophore; (b) obtaining patient mutation data corresponding to detecting genetic or epigenetic mutation by quantifying at least one of allele loss and allele loss and duplication events by measuring the presence of the marker using a flow cytometer configured for detecting the presence of the one or more markers associated with M-antibodies and N-antibodies that have reacted with the sample erythrocyte cells; and (c) comparing the patient mutation data with known mutation data obtained using steps (a) and (b), but using erythrocyte cells removed from patients having a known complex multifactorial disease, to diagnose the known complex multifactorial disease in the patient.

In a yet further embodiment of the disclosure, a method for detection and quantification of somatic "mutations" of Glycophorin A associated with an autism disorder, the method comprises providing blood samples from subjects diagnosed with an autism disorder; the blood samples containing erythrocyte cells; providing control samples having known phenotypes; performing an MN blood group typing on the blood samples; isovolumetrically sphering the blood samples; labeling M alleles and N alleles expressed on surfaces of the erythrocyte cells by contacting the blood samples with anti-M antibodies and anti-N antibodies; detecting and quantifying labeled M alleles and labeled N alleles; comparing labeled M alleles and labeled N alleles found in the blood samples to labeled M alleles and labeled N alleles found in the control samples; detecting and quantifying cells with variant phenotypes consistent with somatic mutations in Glycophorin A; and analyzing data to determine if the frequencies of somatic mutations in Glycophorin A are associated with an autism disorder.

In an embodiment thereof, detecting any somatic mutations in Glycophorin A includes detecting loss or functional inactivation of one Glycophorin A allele.

In another embodiment of the disclosure, a system for detection and quantification of somatic mutations of Glycophorin A associated with an autism disorder, the system comprises means for performing an MN blood group typing on blood samples, the blood samples from subjects diagnosed with an autism disorder; the blood samples containing erythrocyte cells; means for isovolumetrically sphering the blood samples; means for labeling M alleles and N alleles expressed on surfaces of the erythrocyte cells by contacting the blood samples with anti-M antibodies and anti-N antibodies; means for detecting and quantifying labeled M alleles and labeled N alleles; means for comparing labeled M alleles and labeled N alleles found in the blood samples to labeled M alleles and labeled N alleles found in control samples, the control samples having known phenotypes; means for detecting any somatic mutations in Glycophorin A; and means for analyzing data to determine if the somatic mutations in Glycophorin A are associated with an autism disorder.

In yet another embodiment of the disclosure, a method for detection and quantification of somatic mutations of Glycophorin A associated with a complex, multifactorial disease, the method comprises providing blood samples from subjects diagnosed with the complex, multifactorial disease; the blood samples containing erythrocyte cells; providing control samples having known phenotypes; performing an MN blood group typing on the blood samples; isovolumetrically sphering the blood samples; labeling M alleles and N alleles expressed on surfaces of the erythrocyte cells by contacting the blood samples with anti-M antibodies and anti-N antibodies; detecting and quantifying labeled M alleles and labeled N alleles; comparing labeled M alleles and labeled N alleles found in the blood samples to labeled M alleles and labeled N alleles found in the control samples; detecting and quantifying cells with variant phenotypes consistent with any somatic mutations in Glycophorin A; and analyzing data to determine whether if the frequency of somatic mutations in Glycophorin A are associated with the complex, multifactorial disease.

In an embodiment thereof, the complex, multifactorial disease is cancer or an autism spectrum disorder.

BRIEF DESCRIPTION OF THE DRAWINGS

A more complete understanding of the present invention may be obtained by references to the accompanying drawings when considered in conjunction with the subsequent detailed description. The embodiments illustrated in the drawings are intended only to exemplify the invention and should not be construed as limiting the invention to the illustrated embodiments.

DETAILED DESCRIPTION OF THE INVENTION

For the purpose of promoting an understanding of the principles of the invention, reference will now be made to embodiments illustrated herein and specific language will be used to describe the same. It will nevertheless be understood that no limitation of the scope of the invention is thereby intended. Any alterations and further modification in the described compositions and methods and any further application of the principles of the invention as described herein, are contemplated as would normally occur to one skilled in the art to which the invention relates.

Other objectives and advantages of this disclosure will become apparent from the following description taken in conjunction with the accompanying drawings, wherein are set forth, by way of illustration and example, certain embodiments of this invention. The drawings constitute a part of this specification and include exemplary embodiments of the present invention and illustrate various objects and features thereof.

As used herein, a "gene mutation" or "genetic mutation" is considered to be any heritable change in the genetic code, despite the fact that "inheritance" is occurring via mitosis rather than meiosis and sexual reproduction.

As used herein, the term "somatic" refers to cells other than the germ or reproductive cells.

A "somatic" mutation refers to mutations occurring in cells other than the germ or reproductive cells. However, epigenetic events inactivating a Glycophorin A allele are also detected. Although "mutation" is not normally used to include such events, genetic nomenclature was designed to describe organismal inheritance, not somatic inheritance, so, by our definition, a stable gene inactivation event that functionally mimics genetic mutations will simply be folded into the overall category of somatic "mutant" or "mutation".

As used herein, the term "allele" refers to one of many forms of a gene responsible for hereditary variation or alternative characteristics. Certain forms of a gene can arise through mutation. There are two alleles at human autosomal loci, one received from each parent. The alleles are in the same relative position on homologous chromosomes.

As used herein, the phrase "allele loss" refers to the functional loss of one allele at a specific locus caused by a deletion mutation or functionally equivalent event. If such a loss occurs in a tumor suppressor gene, neoplastic transformation may result.

As used herein, the phrase "complex, multifactorial human disease" refers to a disease having both genetic and environmental elements in its etiology. Cancer and autism are two non-limiting examples of complex, multifactorial diseases.

As used herein, the term "cancer" refers to any malignant and/or invasive growth or tumor caused by abnormal or uncontrolled cell division.

As used herein, the term "autism" refers to a developmental spectrum disorder appearing during the first years of life and characterized by severe deficits in social interaction and communication and by abnormal behavior patterns, such as the repetition of specific movements or a tendency to focus on certain objects. Autism is not a single particular disorder, but rather includes a spectrum of disorders.

Autism is a "disease of civilization" i.e. it is increasing in frequency in industrialized nations. This increase suggests that autism may be driven by toxic exposures endemic to such industrialization.

Generally, the instant disclosure concerns an analysis of allele loss and somatic gene mutation in complex, multifactorial diseases (i.e. diseases that can have a genetic and/or an environmental etiology). An allele loss somatic mutation assay is relevant for genetic origin or environmental role in multifactorial disease, such as cancer and/or multifactorial disease of development, such as autism or autism spectrum disorders.

Induction of human disease is believed to be caused by genetic predisposition or environmental exposure, but in reality it is more often a combination of both genetics and environment. The present disclosure integrates life-long exposures and genetic modifiers to provide a single biomarker of disease risk.

In humans, in accordance with the disclosure, gene mutations in somatic cells likely underlie a variety of pathological and developmental processes, such as cancer and autism. However, one can be born with these mutations, resulting in rare hereditary disease, or they can be accumulated over a lifetime, accounting for common sporadic disease.

Assays for in vivo mutations in indicator genes are useful tools in genetic toxicology (genotoxicity) and disease risk assessment. Such assays may allow quantitative and qualitative assessments of adverse effects in human populations, and may even enable identification of the nature of toxic exposures. In vivo mutagenicity studies may identify heterogeneity of susceptibility among humans for specific or classes of mutagens or carcinogens. In accordance with the disclosure, relating in vivo mutations in indicator genes to occurrences of subsequent complex diseases such as cancer and autism is carried out. Estimates of relative risk may be made for individuals exposed to deleterious environmental agents, providing a basis for medical intervention such as removal from the source, early diagnosis, and/or early treatment. For background regarding somatic mutations and pathological and toxicological significance, see Chapter 9, section 9.1.1 of *Methods to Assess DNA Damage and Repair: Interspecies Comparisons*, edited by R. G. Tardiff et al., published by John Wiley & Sons Ltd, 1994.

Traditionally, toxicology has involved a search for one or a few agents associated with induction of a disease. In accordance with the disclosure, without being bound to any particular theory, complex, multifactorial diseases are indicated to be caused by the cumulative effect of many small exposures, all contributing to the same toxic effect. This multifactorial approach allows for the screening of patients for a functional response to multiple agents known to be associated with disease.

With regard to cancer, rather than focusing on identifying a single carcinogen, a multi-step model of cancer provides an alternative approach for human carcinogenesis—analysis of humans themselves. If multiple events are required to induce cancer, and most, if not all events are mutations, then cancer should occur differentially in individuals and populations with high frequencies of mutation. S. G. Grant *J Carcinogene Mutagene* 3(1):e106 2012.

The Glycophorin A (GPA) assay is an intermediate biomarker of biological effect, meaning that it integrates both exposure and biological response. It may be applied to populations with a known or suspected genotoxic exposure, to patients with hereditary syndromes causing predisposition to cancer or premature aging, and to patients manifesting a disease endpoint; i.e. cancer or autism. N. T. Myers and S. G. Grant *Methods Mol Biol* 1105:223-244, 2014.

In accordance with the disclosure, since the Glycophorin A (GPA) gene is commonly expressed and easily obtainable from erythrocyte membranes, it is used as a reporter gene for measuring somatic mutations. Flow cytometry is used, as described herein, to detect mutations in these genes, such as allele loss events.

The Glycophorin A (GPA) in vivo somatic mutation assay concurrently detects and quantifies two types of erythrocytes with variant phenotypes at the autosomal locus responsible for the polymorphic MN blood group. The assay utilizes a pair of allele-specific monoclonal antibodies and flow cytometry to analyze a standard population of 5 million cells efficiently. The two phenotypes detected are simple allele loss or allele loss followed by reduplication of the remaining allele. Both phenotypes are consistent with the mechanisms underlying "loss of heterozygosity" at tumor suppressor genes (recessive cancer genes). N. T. Myers and S. G. Grant *Methods Mol Biol* 1105:223-244, 2014.

In accordance with the disclosure, the Glycophorin A allele loss assay is applied to risk assessment and early detection of complex, multifactorial (having both genetic and environmental elements) human diseases, including, but not limited to, cancer and autism spectrum disorders. These diseases sometimes have a germline inheritance aspect in their etiology. Alternatively, these diseases can have an environmental etiology in the sense that various factors (chemicals, radiation, etc.) in the environment can ultimately mutate DNA or create changes that can mimic mutation. It can be extremely difficult to distinguish between these scenarios and the Glycophorin A allele loss assay provides valuable data to determine whether either of these possibilities have occurred, or whether these are contributing to the pathology of these complex diseases. The character of the allele loss obtained can provide this information (based on the profiles of some rare diseases such as recessive DNA repair disorders).

In accordance with the disclosure, the Glycophorin A allele loss assay detects exposure that can cause mutations, which are usually associated with cancer. The data presented herein show that the mutations are also associated with autism and/or autism spectrum disorders. The association with somatic mutation and autism is currently unprecedented in the scientific literature.

The present invention generally concerns the study of in vivo somatic cell gene mutations. In accordance with the disclosure, application of the Glycophorin A allele loss assay is used for risk assessment and early detection of complex, multifactorial (having both genetic and environmental elements) human diseases, including, but not limited to, cancer and autism spectrum disorders.

Since the Glycophorin A (GPA) gene is commonly expressed and easily obtainable from erythrocyte membranes, it is used as a reporter gene for measuring somatic mutations.

Specifically, the Glycophorin (GPA) in vivo somatic mutation assay concurrently detects and quantifies two types of erythrocytes with variant phenotypes at the autosomal locus responsible for the polymorphic MN blood group. The assay utilizes a pair of allele-specific monoclonal antibodies and flow cytometry to analyze a standard population of 5 million cells efficiently. The two phenotypes detected are simple allele loss and allele loss followed by reduplication of the remaining allele. Both phenotypes are consistent with the mechanisms underlying "loss of heterozygosity" at tumor suppressor genes. N. T. Myers and S. G. Grant *Methods Mol Biol* 1105:223-244, 2014.

For the experiments described herein, the Glycophorin A (GPA) in vivo somatic mutation assay was carried out using a recently developed, improved version of the assay protocol as set forth by the inventor, Stephen Grant, in *Methods Mol Biol* 1105:223-244, 2014. These improvements include performance on an improved commercially available platform (BD FACSJazz) and the quantification of allele loss mutants from individuals of homozygous MM and NN genotype.

Figure 1:
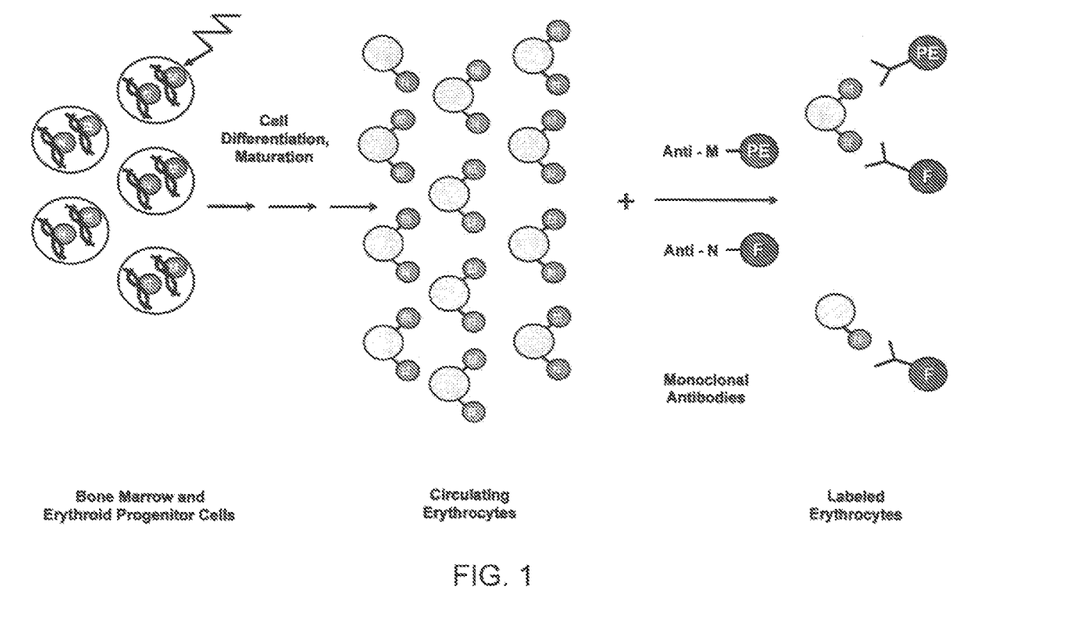
FIG. 1 depicts the discrimination of mutant cells among antibody-labeled erythrocytes; the basis of the Glycophorin A in vivo somatic mutation assay.

The basis of the assay is shown in FIG. 1. Erythroid progenitor cells are formed in the bone marrow, undergo cellular differentiation, and mature into circulating erythrocytes, that have extruded their nuclei and are no longer subject to genetic or epigenetic alteration. The mature, circulating erythrocytes express the M antigen and/or N antigen on the cellular surface. The erythrocytes are then conjugated with antibodies raised against the M and N antigens. The antibodies then bind the antigens on the cellular surface to provide the label that is then analyzed by flow cytometry.

Figure 2:
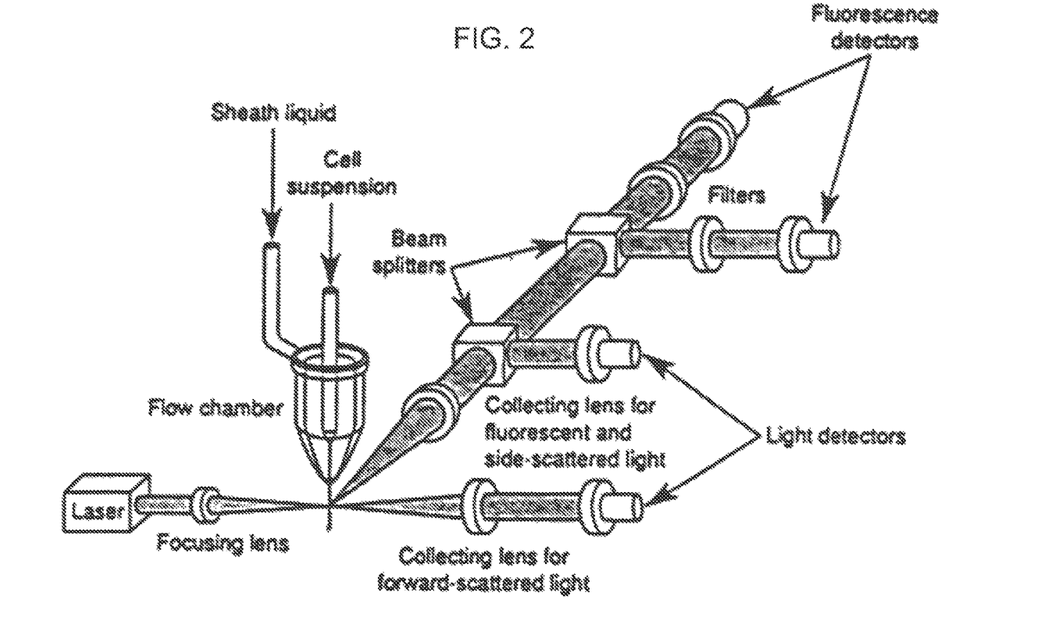
FIG. 2 depicts a flow cytometry apparatus used in the described methods to allow high-throughput and detection of rare events.

Flow cytometry was used in the Glycophorin A in vivo somatic mutation assay because it can detect and quantify mutations, that are extremely rare events, quickly and at relatively low cost. An apparatus for carrying out flow cytometry is illustrated in the sketch of FIG. 2. Flow cytometry works by quantifying the fluorophores labeling individual cells. The apparatus can simultaneously quantify multiple fluorophores on individual cells at a speed of 10,000 cells/second.

A flow cytometric analysis identifies mechanisms responsible for creating mutant cells. Simple loss or inactivation of one Glycophorin A allele will result in cells that label with a single color at the same intensity as parental heterozygous cells: N/Ø cells. A more complicated type of mutant cell arises when loss of one allele at the Glycophorin A locus is accompanied by duplication of the remaining of the two alleles. Cells express the remaining Glycophorin A protein at twice the level of intensity as the parental MN heterozygous cells: N/N cells.

Glycophorin A mutation frequencies increase after exposure to genotoxic agents; for example ionizing radiation, cancer chemotherapy, and smoking. Almost all responses to these agents occur in the allele loss class of variants.

Figure 3:
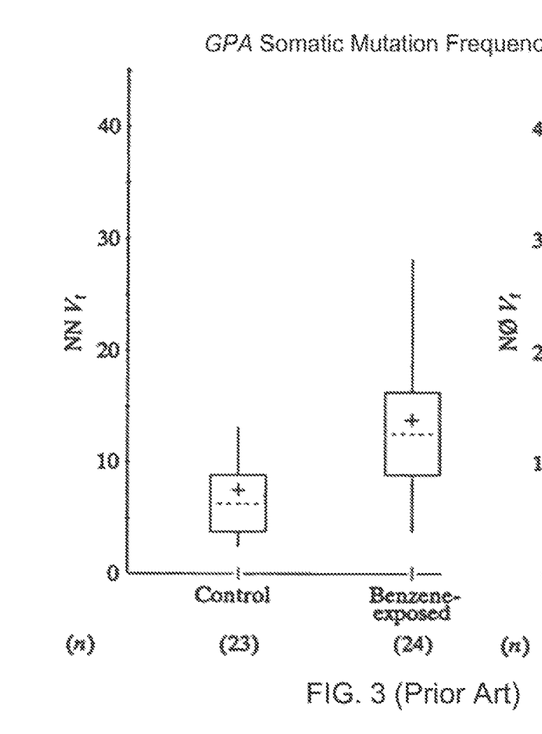
FIG. 3 is a graph of the Prior Art showing Glycophorin (GPA) somatic mutation frequencies after benzene exposure.

The only agent known to date to induce elevated Glycophorin A mutation frequencies occurring as allele duplication is benzene. Mutation frequencies after benzene exposure are shown in the graph of FIG. 3. Rothman et al. *PNAS* 92:4069-4073 1995. Benzene is a common soil pollutant in the U.S., as it was an additive in gasoline until "unleaded" gasoline became the industry standard. Benzene is also a known cause of leukemia. The autistic patients had elevated mutation frequencies in this category. Benzene is the only known chemical that causes changes in that category of mutation. The DNA repair deficient diseases WS, FA and BS all have increases in BOTH allele loss and loss and duplication, therefore, in accordance with the disclosure, this pattern in autism is almost unique, and can be useful in the detection of disease.

Figure 4:
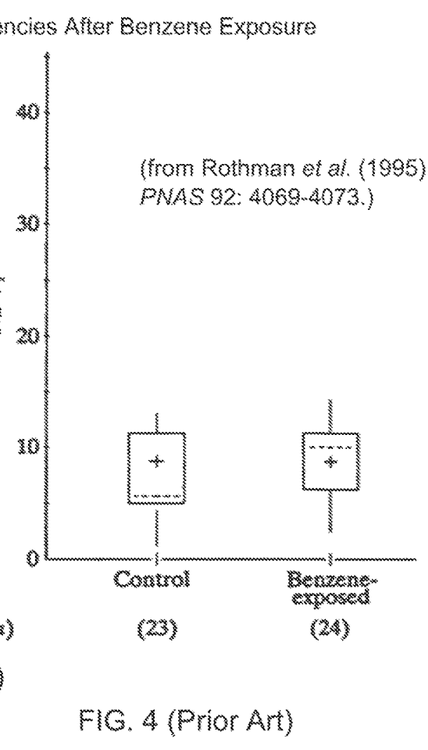
FIG. 4 is a graph of the Prior Art showing age distribution of Glycophorin (GPA) high mutation frequency outliers.

High baseline Glycophorin A mutation frequencies in the patients having autism spectrum disorders are driven by the presence of three outliers. Such individuals have been seen before in normal populations, but they are usually individuals 50 years old or more. The age distribution of Glycophorin A high mutation frequency outliers is shown in the graph of FIG. 4. Bigbee et al. *Mutation Research* 397:119-136 1998.

Figure 5:
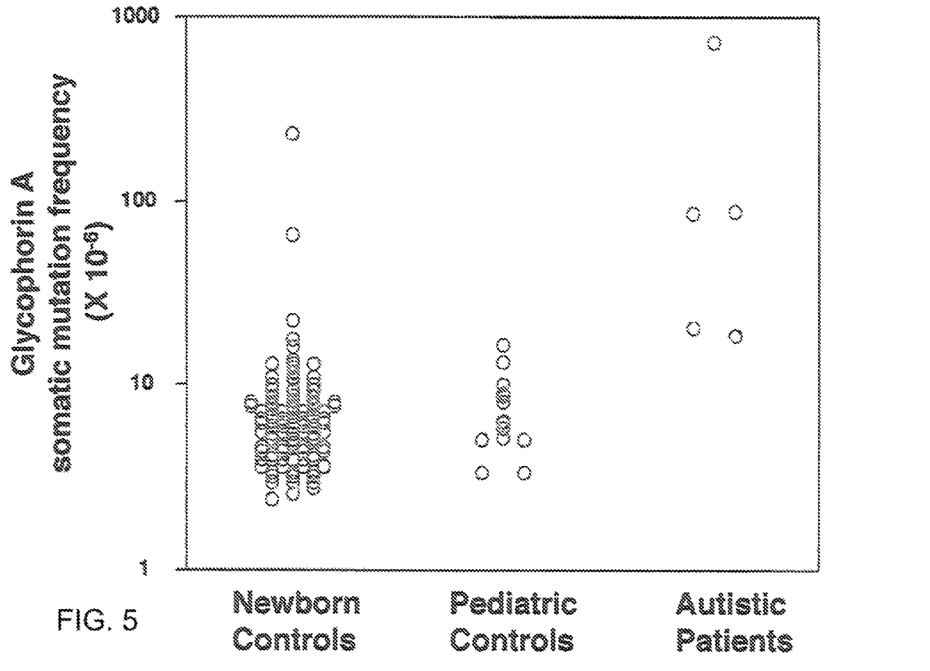
FIG. 5 is a graph showing, in accordance with the disclosure, Glycophorin A somatic mutation frequency ($\times 10^6$) in autistic patients compared to mutation frequencies in both newborn and pediatric controls.
Figure 6:
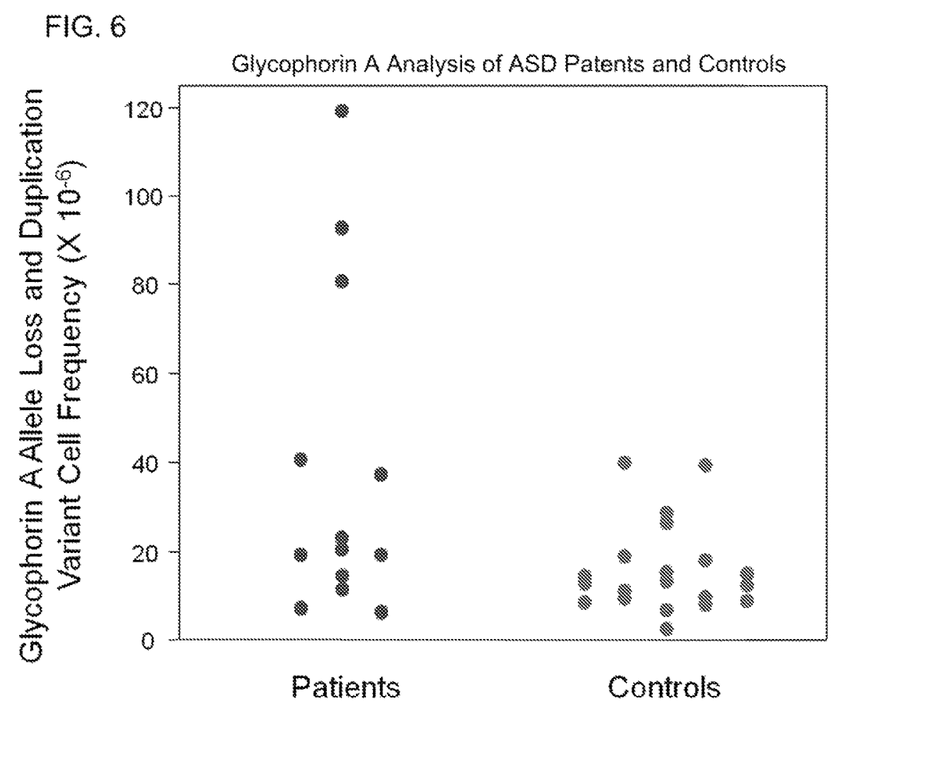
FIG. 6 is a graph showing, in accordance with the disclosure, Glycophorin A allele loss and duplication variant cell frequencies ($\times 10^6$) in autistic patients and age-matched controls.

Results of assays conducted in accordance with the disclosure are shown in FIGS. 5 and 6. Blood samples were obtained from autistic children and age-matched controls from the Children's Institute of Pittsburgh, Pa.

FIG. 5 shows Glycophorin A somatic mutation frequency in autistic children as compared to newborn and pediatric controls. In accordance with the disclosure, the mutation frequency is seen to be higher in the autistic patients.

FIG. 6 shows Glycophorin A allele loss and duplication variant cell frequency in autistic patients as compared to controls. In accordance with the disclosure, the duplication frequency is seen to be exceedingly higher in the autistic patients.

Life history considerations can be incorporated into the interpretation of the assay data. Critical windows of exposure and/or critical tissue-specific sensitivities may determine the health outcome of common exposures.

Blood analyses on 276 elements and chemicals in the blood of these patients are being conducted. This may determine whether any of the specific elements or chemicals are responsible for the observed increased mutation frequencies.

Figure 7:
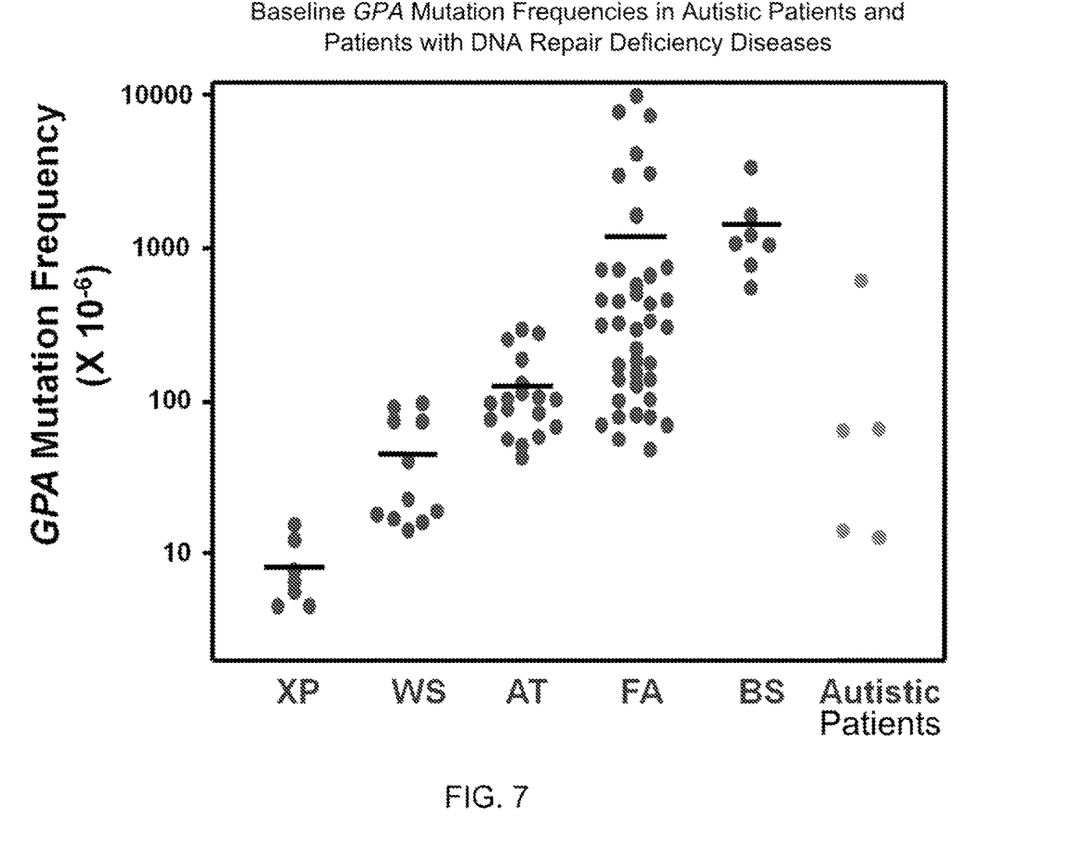
FIG. 7 is a graph showing, in accordance with the disclosure, baseline Glycophorin A mutation frequencies ($\times 10^6$) in autistic patients and in patients diagnosed with various DNA repair deficiency diseases.

In addition to normal controls, baseline Glycophorin A mutation frequencies in autistic patients were compared to patients with DNA repair deficiency diseases (FIG. 7). This experiment puts autistic samples into the context of some known DNA repair deficiency diseases. The DNA repair deficiency diseases are recessive, genetic conditions (orphan diseases). Patients with such diseases require far lower environmental genotoxic exposures to exhibit high levels of somatic mutation than normal individuals. Many of these diseases are associated with an extremely high incidence of cancer or a high incidence of catastrophic, premature aging.

There can be many modulaters/modifiers of response to environment exposures. DNA repair deficiency diseases are meant to represent host factors (human hereditary effects) that modulate response to environmental exposures.

XP refers to Xeroderma Pigmentosum which includes skin cancer at a very young age wherever sunlight touches the skin, the UV sensitivity is due to low nucleotide excision repair; WS refers to Werner's Syndrome which manifests in premature aging and death by age 20; AT refers to Ataxia Telangiectasia which includes damage and cancer after ordinary X-rays due to ionizing radiation repair insufficiency; FA refers to Fanconi Anemia which includes leukemia at a young age due to lack of ionizing radiation repair deficiency; and BS refers to Bloom's Syndrome which includes leukemia and lymphoma at a young age due to several kinds of DNA repair deficiency.

Three out of the 5 autistic samples look abnormal, having higher somatic mutation than the controls, and look more like samples from the orphan diseases.

Further, in accordance with the disclosure, detecting somatic mutations in Glycophorin A includes detecting loss of expression of one Glycophorin A allele or the functional mimicking of this event via epigenetic allele-specific gene inactivation.

Exemplary Computer System

Herein, the terms "controller", "computer", "server", "client", "computer system", "computing system", "personal computing system", or "processing system" describe examples of a suitably configured processing system adapted to implement one or more embodiments of the present disclosure. Any suitably configured processing system is similarly able to be used by embodiments of the present disclosure, for example and not for limitation, a personal computer, a laptop computer, a tablet computer, a personal digital assistant, a workstation, or the like. A processing system may include one or more processing systems or processors. A processing system can be realized in a centralized fashion in one processing system or in a distributed fashion where different elements are spread across several interconnected processing systems.

The terms "computing system", "computer system", and "personal computing system", describe a processing system that includes a user interface and which is suitably configured and adapted to implement one or more embodiments of the present disclosure. The terms "network", "computer network", "computing network", and "communication network", describe examples of a collection of computers and devices interconnected by communications channels that facilitate communications among users and allows users to share resources.

The present subject matter can be realized in hardware, software, or a combination of hardware and software. A system can be realized in a centralized fashion in one computer system, or in a distributed fashion where different elements are spread across several interconnected computer systems. Although one system will now be described, any kind of computer system, or other apparatus adapted for carrying out the methods described herein, is suitable.

Figure 8:
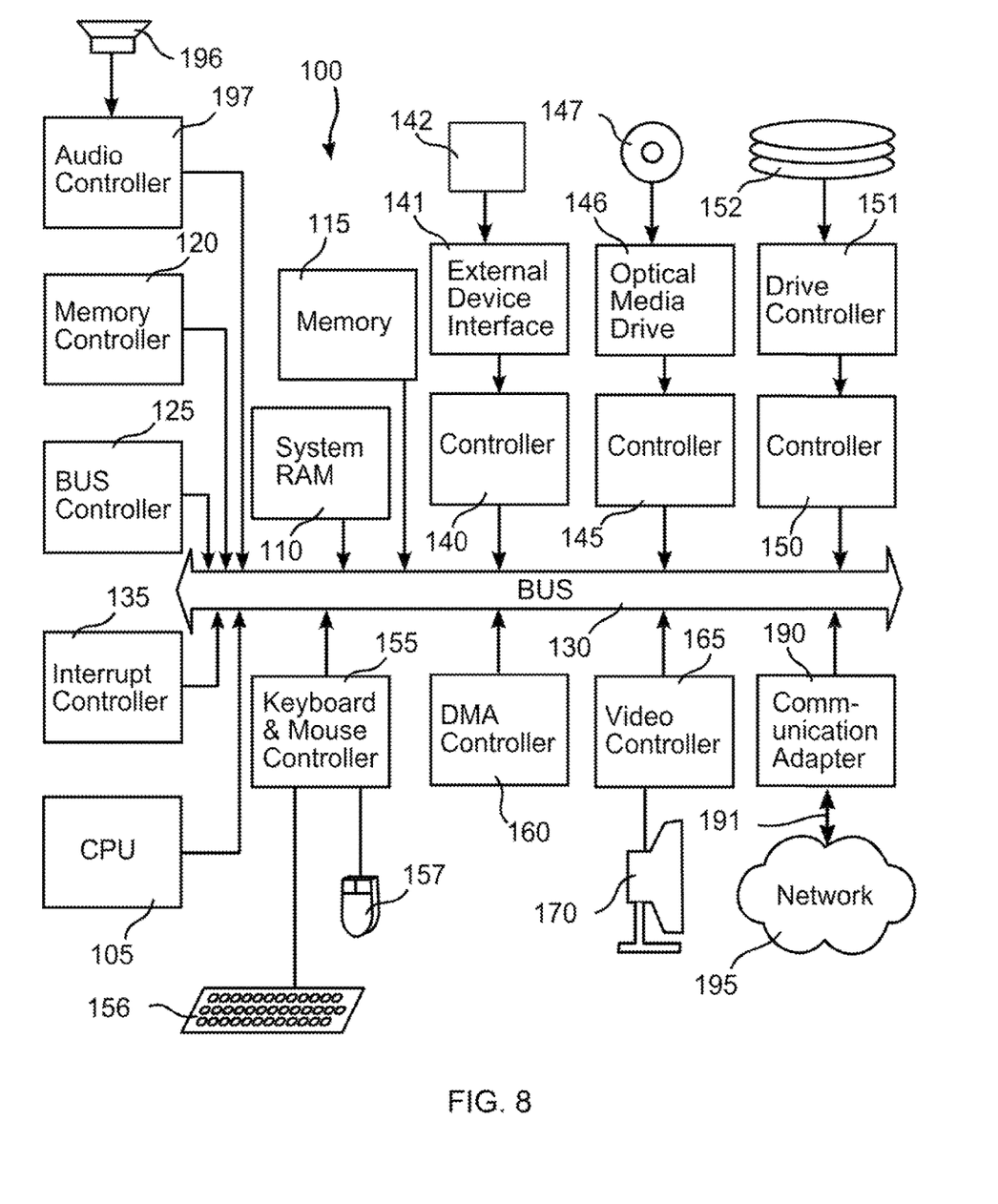
FIG. 8 shows a computer system with which the disclosure may be implemented.

FIG. 8 illustrates the system architecture for a computer system 100 such as a server, work station, embedded system, avionics system, or other processor on which the disclosure may be implemented. The exemplary computer system of FIG. 8 is for descriptive purposes only. Although the description may refer to terms commonly used in describing particular computer systems, the description and concepts equally apply to other systems, including systems having architectures dissimilar to FIG. 8.

Computer system 100 includes at least one central processing unit (CPU) 105, or server, which may be implemented with a conventional microprocessor, a random access memory (RAM) 110 for temporary storage of information, and a read only memory (ROM) 115 for permanent storage of information. A memory controller 120 is provided for controlling RAM 110.

A bus 130 interconnects the components of computer system 100. A bus controller 125 is provided for controlling bus 130. An interrupt controller 135 is used for receiving and processing various interrupt signals from the system components.

Mass storage may be provided by diskette 142, CD or DVD ROM 147, flash or rotating hard disk drive 152. Data and software, may be exchanged with computer system 100 via removable media such as diskette 142 and CD ROM 147. Diskette 142 is insertable into diskette drive 141 which is, in turn, connected to bus 130 by a controller 140. Similarly, CD ROM 147 is insertable into CD ROM drive 146 which is, in turn, connected to bus 130 by controller 145. Hard disk 152 is part of a fixed disk drive 151 which is connected to bus 130 by controller 150. It should be understood that other storage, peripheral, and computer processing means may be developed in the future, which may advantageously be used with the disclosure.

User input to computer system 100 may be provided by a number of devices. For example, a keyboard 156 and mouse 157 are connected to bus 130 by controller 155. An audio transducer 196, which may act as both a microphone and a speaker, is connected to bus 130 by audio controller 197, as illustrated. It will be obvious to those reasonably skilled in the art that other input devices, such as a pen and/or tablet, Personal Digital Assistant (PDA), mobile/cellular phone and other devices, may be connected to bus 130 and an appropriate controller and software, as required. DMA controller 160 is provided for performing direct memory access to RAM 110. A visual display is generated by video controller 165 which controls video display 170. Computer system 100 also includes a communications adapter 190 which allows the system to be interconnected to a local area network (LAN) or a wide area network (WAN), schematically illustrated by bus 191 and network 195.

Operation of computer system 100 is generally controlled and coordinated by operating system software, such as a Windows system, commercially available from Microsoft Corp., Redmond, Wash. The operating system controls allocation of system resources and performs tasks such as processing scheduling, memory management, networking, and I/O services, among other things. In particular, an operating system resident in system memory and running on CPU 105 coordinates the operation of the other elements of computer system 100. The present disclosure may be implemented with any number of commercially available operating systems.

One or more applications, such as an HTML page server, or a commercially available communication application, may execute under the control of the operating system, operable to convey information to a user.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not intended to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The methods, procedures, and techniques described herein are presently representative of the preferred embodiments, are intended to be exemplary and are not intended as limitations on the scope. Changes therein and other uses will occur to those skilled in the art which are encompassed within the spirit of the invention. Although the invention has been described in connection with specific, preferred embodiments, it should be understood that the invention as ultimately claimed should not be unduly limited to such specific embodiments. Indeed various modifications of the described modes for carrying out the invention which are obvious to those skilled in the art are intended to be within the scope of the invention.

What is claimed is:

1. A method for detecting a specific complex multifactorial disease based on allele loss and somatic gene mutations in a subject being tested for the complex multifactorial disease, the method comprising:
    performing an MN blood group typing on a first blood sample of the subject;
    performing an MN blood group typing on a second blood sample of a control subject having a known MN blood group phenotype;
    isovolumetrically sphering erythrocytes from the first and second blood samples;
    differentially labeling M alleles and N alleles expressed on a surface of each of the erythrocytes by contacting the erythrocytes from the first and second blood samples with anti-M antibodies and anti-N antibodies;
    detecting and quantifying each labeled M allele and labeled N allele expressed on the surface of each of the erythrocytes from the first and second blood samples;
    making a comparison between the first and the second blood samples by comparing presence and quantity of each labeled M allele and labeled N allele found on the surface of each of the erythrocytes from the first blood sample to presence and quantity of each labeled M allele and labeled N allele found on the surface of each of the erythrocytes from the second blood sample;
    detecting and quantifying erythrocytes having variant phenotypes based on the presence and quantity of each labeled M allele and labeled N allele found on the surface of each of the erythrocytes to identify somatic mutations in Glycophorin A for each of the first blood sample and the second blood sample;
    calculating frequency of somatic mutations in Glycophorin A in the first blood sample and in the second blood sample based on erythrocytes identified as having variant phenotypes; and
    detecting the specific complex multifactorial disease based on allele loss and somatic gene mutations by comparing the frequency of somatic mutations in Glycophorin A found in the first blood sample to a frequency of somatic mutations in Glycophorin A in a subject known to have the specific complex multifactorial disease, wherein a match of the frequency of somatic mutations of Glycophorin A found in the first blood sample to the frequency of somatic mutations of Glycophorin A in the subject known to have the specific complex multifactorial disease detects the presence of the complex multifactorial disease in the subject being tested for the specific complex multifactorial disease.

2. The method according to claim 1, further comprising age-matching the subject known to have the specific complex multifactorial disease with the subject being tested for the specific complex multifactorial disease and with the control subject.

3. The method according to claim 1, wherein the labeling of M alleles and N alleles includes contacting the erythrocytes from the first and second blood samples with fluorescently-labeled anti-M antibodies and fluorescently-labeled anti-N antibodies.

4. The method according to claim 1, wherein the detecting and quantifying each labeled M allele and labeled N allele is carried out using flow cytometry.

5. The method according to claim 1, wherein the calculating frequency of somatic mutations in Glycophorin A includes quantifying erythrocytes having a somatic mutation in Glycophorin A.

6. The method according to claim 1, wherein the calculating frequency of somatic mutations in Glycophorin A includes quantifying erythrocytes having an allele-loss phenotype.

7. The method according to claim 1, wherein the calculating frequency of somatic mutations in Glycophorin A includes obtaining a mutation frequency of Glycophorin A alleles.

8. The method according to claim 1, wherein the calculating frequency of somatic mutations in Glycophorin A includes quantifying erythrocytes having variant MN blood group phenotypes consistent with loss of one Glycophorin A allele.

9. The method according to claim 1, wherein the calculating frequency of somatic mutations in Glycophorin A includes quantifying erythrocytes having variant MN blood group phenotypes consistent with loss or functional inactivation of one Glycophorin A allele and duplication of a remaining Glycophorin A allele.

10. The method according to claim 1, wherein the calculating frequency of somatic mutations in Glycophorin A includes quantifying erythrocytes having variant MN blood group phenotypes consistent with loss of expression of one Glycophorin A allele or functional mimicking of the loss of expression of one Glycophorin A allele via epigenetic allele-specific gene inactivation.

11. The method according to claim 1, wherein the method for detecting a specific complex multifactorial disease is a method for detecting a DNA repair deficiency disease.

12. The method according to claim 1, wherein the method for detecting a specific complex multifactorial disease is a method for detecting cancer.

13. A method for detecting an autism spectrum disorder based on allele loss and somatic gene mutations in a subject being tested for the autism spectrum disorder, the method comprising:
performing an MN blood group typing on a first blood sample of the subject;
performing an MN blood group typing on a second blood sample of a control subject having a known MN blood group phenotype;
isovolumetrically sphering erythrocytes from the first and second blood samples;
differentially labeling M alleles and N alleles expressed on a surface of each of the erythrocytes by contacting the erythrocytes from the first and second blood samples with anti-M antibodies and anti-N antibodies;
detecting and quantifying each labeled M allele and labeled N allele expressed on the surface of each of the erythrocytes from the first and second blood samples;
making a comparison between the first and the second blood samples by comparing presence and quantity of each labeled M allele and labeled N allele found on the surface of each of the erythrocytes from the first blood sample to presence and quantity of each labeled M allele and labeled N allele found on the surface of each of the erythrocytes from the second blood sample;
detecting and quantifying erythrocytes having variant phenotypes based on the presence and quantity of each labeled M allele and labeled N allele found on the surface of each of the erythrocytes to identify somatic mutations in Glycophorin A for each of the first blood sample and the second blood sample;
calculating frequency of somatic mutations in Glycophorin A in the first blood sample and in the second blood sample based on erythrocytes identified as having variant phenotypes; and
detecting the autism spectrum disorder based on allele loss and somatic gene mutations by comparing the frequency of somatic mutations in Glycophorin A found in the first blood sample to a frequency of somatic mutations in Glycophorin A in a subject known to have the autism spectrum disorder, wherein a match of the frequency of somatic mutations of Glycophorin A found in the first blood sample to the frequency of somatic mutations of Glycophorin A in the subject known to have the autism spectrum disorder detects the presence of the autism spectrum disorder based on allele loss and somatic gene mutations in the subject being tested for the autism spectrum disorder.

14. The method according to claim 13, further comprising age-matching the subject known to have the autism spectrum disorder with the subject being tested for the autism spectrum disorder and with the control subject.

15. The method according to claim 13, wherein the labeling of M alleles and N alleles includes contacting the erythrocytes from the first and second blood samples with fluorescently-labeled anti-M antibodies and fluorescently-labeled anti-N antibodies.

16. The method according to claim 13, wherein the detecting and quantifying each labeled M allele and labeled N allele is carried out using flow cytometry.

17. The method according to claim 13, wherein the calculating frequency of somatic mutations in Glycophorin A includes quantifying erythrocytes having a somatic mutation in Glycophorin A.

18. The method according to claim 13, wherein the calculating frequency of somatic mutations in Glycophorin A includes quantifying erythrocytes having an allele-loss phenotype.

19. The method according to claim 13, wherein the calculating frequency of somatic mutations in Glycophorin A includes obtaining a mutation frequency of Glycophorin A alleles.

20. The method according to claim 13, wherein the calculating frequency of somatic mutations in Glycophorin A includes quantifying erythrocytes having variant MN blood group phenotypes consistent with loss of one Glycophorin A allele.

21. The method according to claim 13, wherein the calculating frequency of somatic mutations in Glycophorin A includes quantifying erythrocytes having variant MN blood group phenotypes consistent with loss or functional inactivation of one Glycophorin A allele and duplication of a remaining Glycophorin A allele.

22. The method according to claim 13, wherein the calculating frequency of somatic mutations in Glycophorin A includes quantifying erythrocytes having variant MN blood group phenotypes consistent with loss of expression of one Glycophorin A allele or functional mimicking of the loss of expression of one Glycophorin A allele via epigenetic allele-specific gene inactivation.

23. A method for detecting a specific complex multifactorial disease based on allele loss and somatic gene mutations in a subject being tested for the complex multifactorial disease, the method comprising:
performing an MN blood group typing on a first blood sample of the subject;
performing an MN blood group typing on a second blood sample of a control subject having a known MN blood group phenotype;
isovolumetrically sphering erythrocytes from the first and second blood samples;
differentially labeling M alleles and N alleles expressed on a surface of each of the erythrocytes by contacting the erythrocytes from the first and second blood samples with anti-M antibodies labeled with a detectable marker and anti-N antibodies labeled with a detectable marker;
detecting and quantifying each labeled M allele and labeled N allele expressed on the surface of each of the erythrocytes from the first and second blood samples by detecting and quantifying the detectable markers;
identifying erythrocytes expressing only an M allele or only an N allele from the first blood sample and the second blood sample and therefrom identifying each of the erythrocytes expressing only the M allele or the N allele as variant erythrocytes having somatic mutations in Glycophorin A;
calculating frequency of the somatic mutations in Glycophorin A by counting a number of the identified variant erythrocytes occurring per number of erythrocytes analyzed from the first blood sample;
calculating frequency of the somatic mutations in Glycophorin A by counting a number of the identified variant erythrocytes occurring per number of erythrocytes analyzed from the second blood sample; and
detecting the specific complex multifactorial disease based on allele loss and somatic gene mutations by comparing the calculated frequency of somatic mutations in Glycophorin A in the first blood sample to a frequency of somatic mutations of Glycophorin A in a subject known to have the specific complex multifactorial disease, wherein a match between the calculated frequency of somatic mutations in Glycophorin A in the first blood sample and the frequency of somatic mutations of Glycophorin A in the subject known to have the specific complex multifactorial disease indicates presence of the specific complex multifactorial disease in the subject being tested for the complex multifactorial disease.

24. The method according to claim 23, further comprising age-matching the subject known to have the specific complex multifactorial disease with the subject suspected of having or being at risk for the specific complex multifactorial disease and with the control subject.

25. The method according to claim 23, wherein the somatic gene mutations in Glycophorin A include loss, functional inactivation, and duplication of an allele of Glycophorin A.

26. The method according to claim 23, wherein the method for detecting a specific complex multifactorial disease is a method for detecting a DNA repair deficiency disease, cancer, or an autism spectrum disorder.

* * * * *